(12) United States Patent
Engelhardt et al.

(10) Patent No.: US 8,708,548 B2
(45) Date of Patent: Apr. 29, 2014

(54) APPARATUS AND METHOD FOR THE DETECTION OF SOLID SUBSTANCES IN A LIQUID PHASE

(75) Inventors: Matthias Engelhardt, Rapperswil (CH); Guido Schuster, Stäfa (CH); Michael Meyer, Islisberg (CH); Bruno Nufer, Illnau (CH)

(73) Assignee: Mettler-Toledo AG, Greifensee (CH)

( * ) Notice: Subject to any disclaimer, the term of this patent is extended or adjusted under 35 U.S.C. 154(b) by 169 days.

(21) Appl. No.: 13/298,611

(22) Filed: Nov. 17, 2011

(65) Prior Publication Data

US 2012/0134230 A1 May 31, 2012

(30) Foreign Application Priority Data

Nov. 25, 2010 (EP) .................................. 10192601

(51) Int. Cl.
*G01N 21/85* (2006.01)
*B01F 1/00* (2006.01)

(52) U.S. Cl.
USPC ............................. 366/142; 356/427; 356/442

(58) Field of Classification Search
USPC .................... 356/426–428, 441, 442; 366/142
See application file for complete search history.

(56) References Cited

U.S. PATENT DOCUMENTS

| 3,576,442 A | * | 4/1971 | Nakamura ................. 250/223 B |
| 3,627,423 A | * | 12/1971 | Knapp et al. .................... 356/340 |
| 3,830,969 A | * | 8/1974 | Hofstein ........................ 348/127 |
| 3,914,058 A | * | 10/1975 | Knapp et al. .................. 356/427 |
| 4,136,930 A | * | 1/1979 | Gomm et al. .................. 348/127 |
| 4,664,521 A | * | 5/1987 | Scott et al. .................. 356/239.4 |
| 4,902,137 A | * | 2/1990 | Krieg et al. .................... 356/427 |
| 5,152,180 A | | 10/1992 | Waldhauer, Jr. |
| 5,694,221 A | * | 12/1997 | Knapp .......................... 356/427 |
| 5,969,810 A | * | 10/1999 | Nicks et al. ................. 356/239.4 |
| 6,006,590 A | | 12/1999 | Wang |
| 6,170,980 B1 | | 1/2001 | Martin |
| 6,866,823 B2 | | 3/2005 | Wardlaw |
| 6,869,570 B2 | | 3/2005 | Wardlaw |
| 6,929,953 B1 | | 8/2005 | Wardlaw |
| 7,021,163 B2 | | 4/2006 | Kyne |
| 7,024,955 B2 | | 4/2006 | Carlson et al. |
| 7,068,365 B2 | | 6/2006 | Hansen et al. |
| 7,234,365 B2 | | 6/2007 | Carlson et al. |
| 2004/0138827 A1 | | 7/2004 | Li et al. |

(Continued)

FOREIGN PATENT DOCUMENTS

WO 03/098199 A1 11/2003
WO 2006/084283 A2 8/2006

*Primary Examiner* — Tony G Soohoo
*Assistant Examiner* — Abbas Rashid
(74) *Attorney, Agent, or Firm* — Standley Law Group LLP

(57) ABSTRACT

An apparatus and a method detect the presence of solid particles in a liquid phase, where an at least partially transparent container encloses the solid particles and the liquid phase. The apparatus includes a camera to make digitized images in the form of arrays of pixels with their associated pixel values. The apparatus also includes an agitator device to hold the container and to impart movements to the container, transmitting kinetic energy to the mixture. The camera is aimed at a transparent portion of the container to take images of the mixture in motion. A processor unit, in electronic communication with the camera, receives and processes the digitized images of the mixture in motion, resulting in the generation of an analytical representation of the solid particles in the liquid. In this manner, the state of dissolution of the solid particles may be determined.

10 Claims, 5 Drawing Sheets

(56) References Cited

U.S. PATENT DOCUMENTS

| | | |
|---|---|---|
| 2008/0165354 A1 | 7/2008 | Rantanen et al. |
| 2009/0192644 A1* | 7/2009 | Meyer et al. ............ 700/109 |
| 2009/0207691 A1 | 8/2009 | Fetvedt |
| 2012/0147182 A1* | 6/2012 | Meyer ..................... 348/143 |

* cited by examiner

APPARATUS AND METHOD FOR THE DETECTION OF SOLID SUBSTANCES IN A LIQUID PHASE

CROSS-REFERENCE TO RELATED APPLICATIONS

This application is entitled to benefit of a right of priority under 35 USC §119 from European patent application EP 10192601.2, which was filed on 25 Nov. 2010, and the content of which is incorporated by reference as if fully recited herein.

TECHNICAL FIELD

The disclosed embodiments concern an apparatus and a method for the detecting solid substances in a liquid phase, wherein the solid substance and the liquid phase are enclosed as a mixture in an at least partially transparent container.

BACKGROUND

A recurring task in many fields of industry, particularly in the areas of production, research and development, is to examine liquids for the presence of solid substances, for example particles of powders, suspended matter, and the like.

A further task is to dissolve solid substances in the form of pastes, powders or granules in a liquid phase. One or more solid substances are measured into a container, and the liquid phase, in most cases water or an organic solvent such as ethanol, is added either by weight or by volume. The concentration of the solution resulting from the dissolution process is critically dependent on whether or not all of the solid substance components have been dissolved.

A number of different methods and systems are used to examine liquids for the presence of solid substances and to monitor dissolution processes. The simplest method is limited to a visual inspection of the liquid under examination. In the preparation of a solution, the mixture of solid substance and liquid phase in a container can be stirred until a periodic visual examination no longer reveals any visible solid components. A further method is based on prior experience as to how long a mixture of a specific solid substance and a specific solvent has to be stirred until the substance is completely dissolved.

These methods are inefficient, because the visual inspection is laborious, and if the stirring time is based on past experience, the dissolution process could take longer than necessary. As an additional problem, the visual inspection is highly susceptible to errors, since human operators are directly involved in most of the process steps.

As a way to minimize the influence of the human operator, a device for the monitoring of dissolution processes of solid substances in a liquid phase is proposed in U.S. Pat. No. 5,152,180 A, wherein the solid substance and the liquid phase are put into a container with a stirrer. The process of dissolution is monitored by sending ultrasonic signals in a wide frequency band from an emitter into the liquid phase and measuring the resonance frequency of the liquid phase by means of a detector. As more and more of the solid substance dissolves, the resonance frequency changes, and this opens the possibility to detect when the dissolution process is finished. When all of the solid substance is dissolved, the resonance frequency stops changing, and the device uses this stable state of the resonance frequency as a signal to indicate the end of the dissolution process.

The device of the foregoing description has the disadvantage that the stirrer can interfere with the measurement of the resonance frequency. Furthermore, substance particles can adhere to the wall of the container above the surface of the liquid and thus not get dissolved. Also, the emitter and the receiver are imbedded in the housing wall of the container and thus come into contact with the solution.

It is therefore the objective to propose an apparatus and a method whereby the detection of solid substances in a liquid phase is made possible or whereby the process of dissolution of a mixture of at least one solid substance and a liquid phase can be monitored without thereby contaminating the apparatus.

SUMMARY

This task is solved by the apparatus and the method described herein for the detection of solid substances in a liquid phase.

An apparatus for the detection of solid substances in a liquid phase includes a camera to make digitized images and a processor unit. The digitized images are recorded as arrays of pixels with their associated pixel values. The solid substance and the liquid phase are enclosed as a mixture in an at least partially transparent container. The term "partially transparent container" in the context of the present application means that at least one portion of the walls that form the container is transmissible to electromagnetic radiation without appreciable absorption. The rest of the container walls are not subject to design restrictions, or they may be designed to support the inventive purpose. The parts used for the apparatus therefore need to be matched to the electromagnetic radiation that is being used. For example, if daylight is used, and if this is sufficient for the illumination of the mixture, there is no compelling need for an illumination device. However, as explained below, an illumination device is advisable for getting the best results.

The apparatus further includes an agitator device to hold the container and to impart movements to the container, whereby kinetic energy is transmitted to the mixture. The main purpose of injecting kinetic energy is to keep the mixture inside the container in motion. Normally, the mixture or the solution will remain in motion for some time after the agitator device has been turned off. As will be described later herein, these movements of the mixture are used for detecting solid matter within a liquid phase.

The injection of kinetic energy can achieve two further purposes. First, due to the intermixing and the turbulent movements, the solid substance is dissolved in the liquid phase more rapidly. Since the container is fully enclosed, it can be tumbled and shaken by the agitator device in all directions so that, as a second purpose, all of the solid particles will come into contact with the liquid phase so that they can be dissolved.

The term "processor unit" in the present context means any device with the capability to process and store digital data, for example a master processor system, a computer or laptop which can be connected to the other parts of the apparatus, or also integrated concepts such as a circuit board with a processor that is arranged in the agitator device, a computer unit that is incorporated in the camera, or a field-programmable gate array (FPGA) with memory modules and a connected input/output unit.

The camera is aimed at a transparent portion of the container to take images of the mixture in motion. During a recording phase, the camera takes digitized images of the mixture in motion and transmits them to the processor unit.

The purpose of taking digitized images is to allow the static portion of the image to be separated from the dynamic portion in the subsequent evaluation process. The static portion includes all parts of the container and the vicinity of the container, while the dynamic image portion covers the mixture that is moving around inside the container.

The simplest way to produce digitized images that are suitable for the evaluation process is realized with an arrangement where the camera is installed in a stationary position and the movement of the container is periodically interrupted by a rest phase. Of course, the camera could also be solidly connected to the container, or it could be moved synchronously with the container during the recording phase, so that the camera tracks every movement of the container during the recording phase. With this second arrangement, the recording phase can take place not only when the container is at rest, but also when it is receiving kinetic energy. According to a third concept, the times when the camera is triggered to take an image can be coupled to a specific position of the container, so that the container always appears in the same position relative to its environment. As a fourth possibility, images of the moving container are taken at random, but this requires considerably more computing capacity for the subsequent evaluation process and is therefore not recommended.

During the recording phase, at least one series of at least two digitized images of the mixture in motion is produced. In order to have these digitized images available for the subsequent evaluation process, they are preferably stored in a temporary memory. With a minimum of two of the digitized images, an analytical representation can be generated of the mixture in motion.

In a first disclosed embodiment, the analytical representation is generated by the processor unit from two digitized images of the same series by subtracting the pixel values of a first image from the pixel values of a second image. The moving solid substance particles of the mixture will appear in the analytical representation as contrast areas, i.e. as areas that are distinguished by having different pixel values.

In a second disclosed embodiment, an intersection of a series of preceding digitized images is calculated. Next, the analytical representation is generated by subtracting the pixel values of the intersection from the pixel values of a digitized image. In this analytical representation, the moving solid components of the mixture appear again as contrast areas, i.e. as areas of different pixel values.

In a third disclosed embodiment, the analytical representation is generated by means of an estimate of the movements of the individual pixels of at least two digitized images, wherein the estimate of the movements will characterize as the static image portion all those pixels whose movement vectors from one image to the other are zero. This entails a comparison of the positions of the individual pixels and their pixel values relative to the neighboring pixels and their pixel values, which requires significantly more computing power. In this analytical representation, the moving solid parts of the mixture appear again as contrast areas, i.e. as areas of different pixel values.

The camera can have a lens or a pinhole diaphragm to project the image of the mixture in motion onto the image plane. The image plane is occupied by a two-dimensional array of radiation sensors. This two-dimensional array of radiation sensors will hereinafter be referred to as sensor element. The sensor elements for electromagnetic radiation come in a broad variety, for example CCD (charge-coupled device) sensors, active-pixel sensors, focal plane arrays, X-ray sensor elements and the like. The two-dimensional image projected into the image plane is captured by the camera in the form of a two-dimensional array of image elements, i.e. pixels, and the data generated for each pixel represent color and luminance. The contributions of the light that is reflected from the different points of the mixture in motion normally make up the pixel value which represents the color and intensity of a specific pixel. Logically, if a gray-scale camera is used, there will be no color data.

As the camera is preferably set up to take an image of the entire container, it is possible that portions of the container are included that make a meaningful evaluation more difficult. As an example, the container could be a bottle of cylindrical cross-section, in which case the curvature of the glass in the peripheral areas of the container will hardly allow an image of the moving mixture that is amenable to evaluation. In principle, however, any container that can be closed can be used, regardless of its shape, if it has at least one transparent portion.

The apparatus and the container can be used for the purpose of an analysis alone, meaning that an unknown liquid is to be investigated for the presence of solids, or that a possible process of dissolution has already taken place and the finished solution that is to be examined is poured into the container which is set into the apparatus. However, a sensible procedure is to prepare the solution in the container itself. The design of the container can be optimized in accordance with its purpose as a mixture-preparation and analysis container, so that the internal contours of the container optimally support the dissolution process of the solid substance in the liquid phase as a result of the injection of kinetic energy. This is possible for example with a design where parts of the container are made narrower, and also by avoiding corners in which "dead zones" could form which would impede the process of dissolution of the solid substance accumulated there. The walls of the container can further be optimized for the optical analysis method. For example, distortion-free areas can be formed in the wall, through which the camera is aimed for taking the digitized images. It is also possible for light-focusing or divergent lenses to be formed in the wall. In principle, any transparent material can be used for the transparent portion, in particular glass and transparent synthetic materials. The choice of a suitable material depends essentially on the selection of the liquid phase, i.e. the solvent, and the properties of the solid substance in its solid and/or dissolved form. The container can further have another transparent portion or an area of reduced opacity in order to optimize the illumination of the mixture under examination.

According to a further developed concept, image portions that contain no useful information can be excluded from the evaluation by selecting at least one evaluation zone within the analytical representation. The evaluation zone is then investigated for contrast areas. Of course it is also possible to select a section out of the first image and out of the second image, respectively, and to generate from these sections an analytical representation that is used as the evaluation zone.

The at least one evaluation zone can further be subdivided into segments of equal or different size. This has the advantage that the individual segments can be evaluated separately, so that smaller batches of data are processed sequentially. Furthermore, by working in segments, a search for local extremes can be made in the subsequent statistical analysis, which makes the apparatus more sensitive in the detection of particles.

The investigation involves the process of evaluating the frequency distribution of the pixel values within an analytical representation or a segment. To eliminate camera-related noise, a predetermined bandwidth of pixel values in the frequency distribution is dropped from consideration in a continued evaluation. The predetermined bandwidth of pixel values can be established for example with a clear reference solution containing no undissolved substance.

The apparatus can further include a source which emits electromagnetic radiation that is matched to the sensor element of the camera. Since commercially available cameras work within the range of visible light and thus represent a cost-effective solution, the apparatus is preferably equipped with at least one illumination device in the form of an area light source. The container, which is kept in motion by the agitator device, can be arranged for example between the area light source and the camera. Thus, the mixture is backlit by the area light source. Of course, in this case the container wall opposite the transparent portion needs to be transparent also, or it should at least be designed with some permeability for light. Obviously, the area light source could also be directed at the container in any spatial arrangement that is selected so that only light that is scattered and/or diverted by the particles of the solid substance arrives at the camera.

In addition to, or instead of, the area light source, the apparatus can be equipped with at least one point light source. The electromagnetic waves, specifically light waves, of the at least one point light source are aimed at the transparent container wall portion that is to be covered by the camera image. The light rays that are reflected, deflected, or partially absorbed by the particles of the mixture are captured by the sensor element of the camera as bright and dark contrast areas and result in pixel values that are distinguishable from the pixel values of the liquid phase.

As explained previously herein, the container is moved by the agitator device. The movements can be oriented in any direction. For example, the agitator device can produce oscillatory movements in the lengthwise direction, swivel or rotate the container, or turn it upside down repeatedly. The only important aspect is that all substance particles should be set in motion, so that they move in relation to the container and can thus be detected. A reliable check for the presence of solid matter in the liquid phase can be performed if no particles adhere to the inside wall of the container. To ensure that all solid substance particles can be reached by the liquid phase and cannot, for example, remain stuck to a wall portion of the container that is not being wetted, the agitator device can be designed so that the container is also rotatable about its lengthwise central axis. The agitator device can also be used for a dissolution process. To reduce wear on the agitator device, the dissolution process or at least a major part of the dissolution process can also occur already before the container is set into the apparatus.

The following method can be used to detect solid substances in a liquid phase. The solid substance and the liquid phase have to be enclosed as a mixture in an at least partially transparent container. The inventive method includes at least the steps that:

the container is subjected to movements, whereby kinetic energy is injected into the mixture, during a recording phase, a series of at least two digitized images of the mixture that is in motion inside the container are taken by means of the camera as arrays of pixels with their associated pixel values, based on the pixel arrays and their associated pixel values, an analytical representation is calculated, wherein the moving solid substance particles appear as contrast areas, i.e. areas distinguished by having different pixel values, and the analytical representation is searched for the presence of contrast areas or areas with different pixel values.

It can be added to the method as a further step, that at least one evaluation zone is selected from the analytical representation. Of course it is also possible to select a section from each of two digitized images of the same series and to generate from these sections an analytical representation that is used as the evaluation zone.

In further steps that can be added to the inventive method, the analytical representation or the at least one evaluation zone is subdivided into segments of equal or different size, and each segment is searched for the presence of contrast areas that are distinguished from the rest of the same segment by having different pixel values.

The analytical representation or a segment can be examined by evaluating its frequency distribution of pixel values. To eliminate camera-related noise, a predetermined bandwidth of pixel values in the frequency distribution is dropped from consideration in a continued evaluation.

The method can include the further steps that the number of segments is determined whose frequency distributions include pixel values outside of the predetermined bandwidth of pixel values, wherein this number of segments represents a measure for the amount of solid matter that is present and/or for the progress of the dissolution process. As an alternative, it is also possible to determine the number of pixel values that are beyond a predefined threshold outside of the bandwidth. The smaller the number of segments that have deviating pixel values, the fewer particles are present in the solution. If only a part of the mixture is examined, it is preferred to take several series of images and to process and evaluate each series in accordance with the foregoing description, in order to be able to draw a reliable conclusion about the state of the mixture under examination. In between the series, the mixture can again be injected with kinetic energy by means of the agitator device.

A more accurate conclusion can be reached with the further steps, that weights are assigned to the segments whose frequency distributions include pixel values outside of the predetermined pixel value bandwidth, and that the weighted numbers of the segments are added to each other, wherein the sum of the numbers likewise represents a measure for the amount of solid matter and/or for the progress of the dissolution process. Using a weighted sum has the effect that for example very dark and very light contrast areas are counted more strongly, because they are indicative of large particles. As is well known, the size of the particles strongly affects the dissolution process and the amount of time needed for it.

BRIEF DESCRIPTION OF THE DRAWINGS

The apparatus and method that encompass the invention are explained hereinafter in more detail with references to the drawings, wherein identical parts are identified with identical reference numbers and wherein.

DETAILED DESCRIPTION

Figure 1:
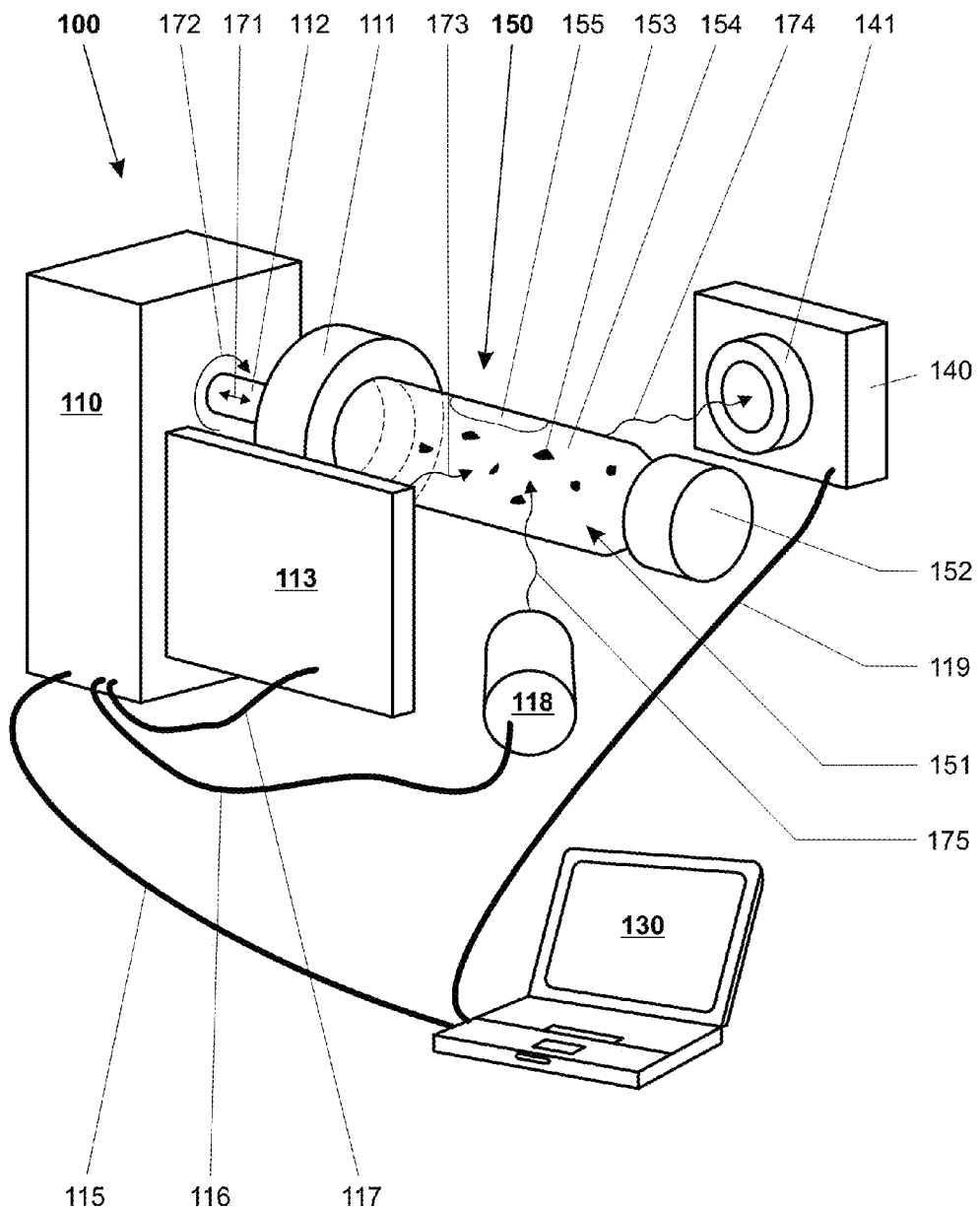
FIG. 1 schematically illustrates an apparatus for detecting a solid substance in a liquid phase, wherein the apparatus includes an agitator device for a container, a camera, an illumination device, and a processor unit.

FIG. 1 schematically illustrates an embodiment of an apparatus 100 for detecting a solid substance 153 in a liquid phase 154. The apparatus 100 includes an agitator device 110 for a container 150 and further includes a camera 140, at least one illumination device 113, 118, and a processor unit 130. The illumination device 113, 118 is not absolutely required, if the solid substance 153 can be distinguished by the camera 140 without it. The solid substance 153 and the liquid phase 154 are put into a container 150 as a mixture. As indicated in the drawing, the container 150 is not filled to capacity; there is also a small gas volume 155 enclosed. The container 150 has a closure device 152 and a bottle-shaped body which is made of a transparent material, for example glass or plastic. Accordingly, the bottle-shaped body also functions as the transparent portion 151 of the container 150. In the operating state of the apparatus 100, the container 150 is oriented with its length extending in the horizontal direction and is releasably connected to a holder socket 111 of the agitator device 110. The holder socket 111 can, for example, consist of a three-jaw chuck or a tension sleeve, in which a portion of the container 150 can be held with a solid grip. Of course, there are also other designs of holder sockets 111 that could be used. Their configuration and functional characteristics will be at the discretion of the designer and will be matched to the containers 150 that are to be used. The holder socket 111 is connected by way of a holder shaft 112 to a drive mechanism (not shown in the drawing), wherein the drive mechanism can generate oscillatory movements 171 in the holder shaft 112 in its lengthwise direction. The drive mechanism can also impart a rotary movement 172 to the holder shaft 112 about its lengthwise central axis. As a result, the liquid phase 154 can reach all areas of the interior space of the container 150, including particles of the solid substance 153 that adhere to the wall of the container 150 in the area of the gas volume 155. Obviously, the arrangement of the container 150 and the movements 171, 172 that are generated by the agitator device 110 are meant only as examples. Of course, one could choose any movements 171, 172 that are suitable to inject kinetic energy into the mixture.

The movements 171, 172, which can also be generated independently of each other, are transmitted from the holder shaft 112 to the holder socket 111 and from the latter to the container 150 that is connected to the holder socket 111. Since the liquid phase 154 and the solid substance 153 are completely surrounded by the container 150, the kinetic energy of the movements 171, 172 is transmitted to the liquid phase 154, so that the solid substance 153 is swirled around in the liquid phase 154. This effect is even enhanced by the presence of the gas volume 155 because, due to the large difference in density between gas and liquid, the liquid phase 154 is significantly easier to agitate than it would be without an enclosed gas volume 155. As a result of this swirling, the solid substance 153 can be dissolved much faster in the liquid phase 154.

When the drive mechanism of the agitator device 110 is switched off and the container 150 as well as the camera 140 are thus in a recording phase, one will find that over an immediately following time span the kinetic energy of the mixture gradually disappears, as can be optically detected from the steadily slowing whirling-around of the solid substance 153. The possibility of optically detecting movements can be used to detect solid matter that is present within the liquid phase or to monitor a process of dissolution, if a series of at least two images of the moving mixture are taken by the camera 140 during the recording phase.

The quality of the images depends essentially on providing the right illumination for the transparent portion 151. In the present example, the container 150 is therefore arranged between an area light source 113 and the camera 140, so that the light waves 173, 174 of the area light source 113 penetrate through the transparent portion 151 of the container 150 and the mixture enclosed in it and can be detected by the lens 141 of the camera 140. A part of the light waves 173, 174 is absorbed, reflected or deflected by the solid substance 153, resulting in contrast areas in the image that appear lighter or darker than the main area of the image which is generated by the light waves 173, 174 that pass through the liquid phase 153.

To illuminate the transparent portion 151 and the moving mixture even better, a point light source 118 or a spotlight may be used in addition to, or instead of, the area light source 113. The light waves 175 of the point light source 118 are preferably oriented at an angle to the image plane of the camera 140, so as to shine more light at the sideways-facing surface areas of the solid particles 153.

The apparatus and the method for the detection of dissolution processes of solid substances 153 in a liquid phase 154 are under the control of a processor unit 130 which is connected to the agitator device 110, the area- and/or point light source 113, 118, and the camera 140 by way of communication lines 115, 116, 117, 119. The latter can be configured as electrical and/or optical cables 115, 116, 117, 119. Of course, control signals and image data can also be communicated through wireless connections between the individual parts of the apparatus 100, in which case every component of the apparatus 100 requires its own power supply. The digital images generated by the camera 140 are transmitted to the processor unit 130, where they are processed and evaluated. Depending on the result of the evaluation, the processor unit 130 can reactivate the drive mechanism of the agitator device 110 in order to dissolve the solid substance 153 or inject the mixture or solution again with kinetic energy and then initiate a further series of digital images as a control measure. Furthermore, based on several series that have been evaluated, it is possible to estimate how much more time the current dissolution process is likely to take.

Figure 2:
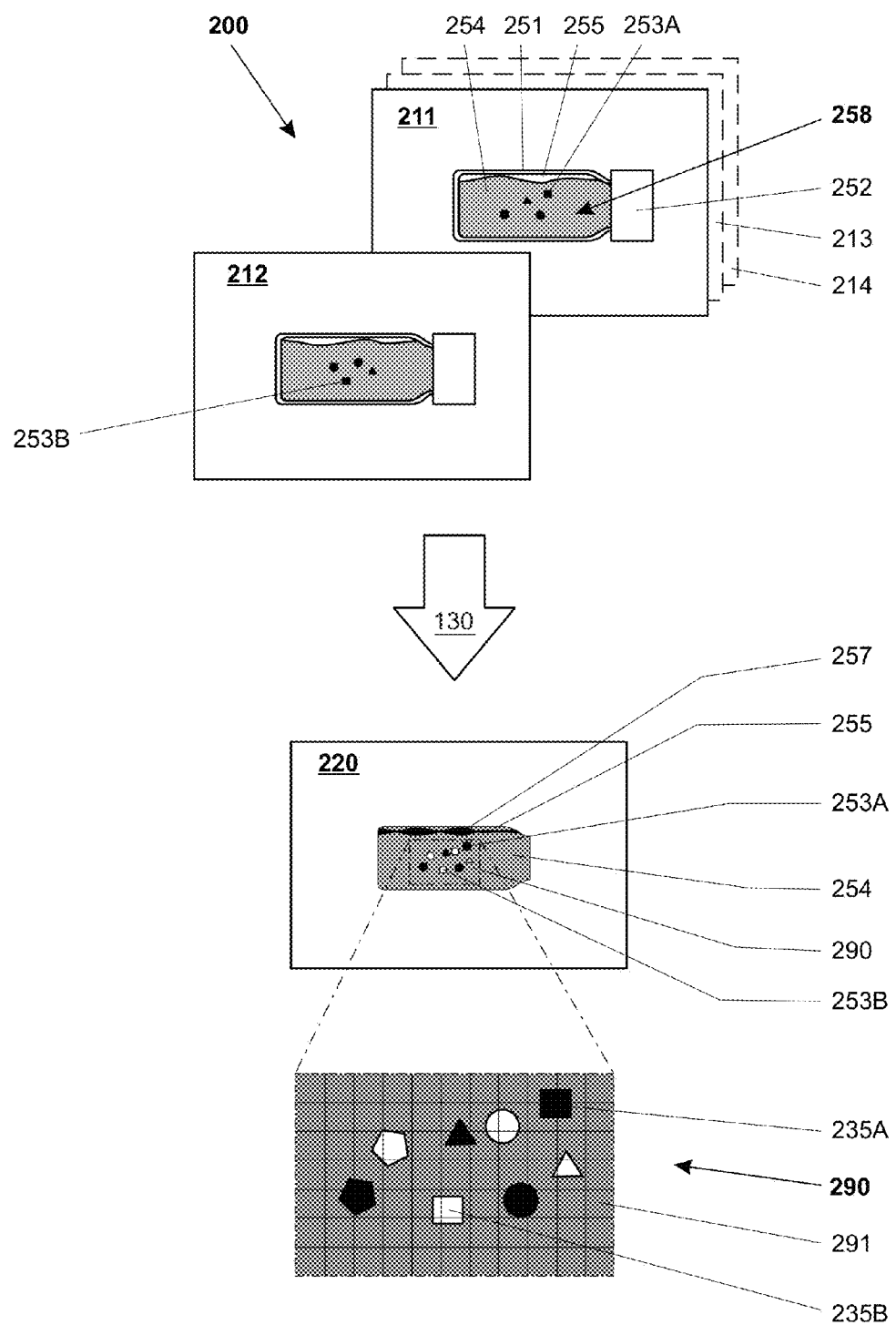
FIG. 2 schematically illustrates the essential steps of producing an analytical representation and subdividing it into segments.

The processing of the digital images generated by the camera 140 is illustrated schematically in FIG. 2. In the recording phase which has been described hereinabove, a series of at least two digital images 211, 212 of the transparent portion 251, more specifically of the mixture 258 which is visible through the transparent wall portion, is taken by means of the camera 140. In the first digital image 211, the mixture 258 of solid matter 253A and liquid phase 254 can be seen, as well as the gas volume 255, the transparent portion 251 configured in the form of a bottle-shaped body, and the closure device 252. The exact same elements as in the first digital image 211 are also shown in the second digital image 212, only with the difference that in the second digital image 212 the positions of the particles of the solid substance 253B have changed in relation to the positions of the particles of the solid substance 253A of the image 211. The individual particles of the solid substance 253A, 253B are recognizable in the two images 211, 212 as contrast areas, whose pixel values are different from the liquid phase 254 which fills out the main area of the image.

In the processor unit 130, which is schematically indicated by the block arrow 130, the pixel values of the second image 212 are subtracted from the pixel values of the first image 211, and an analytical representation 220 is generated with the pixel values resulting from the subtraction.

According to its nature of representing the difference of the pixel values, the analytical representation 220 has twice the number of contrast areas, unless there are overlaps between the positions of individual contrast areas. The contrast areas of the solid substance 253A of the first image 211 stand out dark against the main area of the liquid phase 254. Also, the intersecting contour area of the liquid surface 257 between the gas volume 255 and the liquid phase 254 stands out dark. The contrast areas of the solid substance 253B of the second image 212 stand out as light areas against the liquid phase 254. To eliminate the intersecting contour area of the liquid surface 257 from entering into the evaluation, an evaluation zone 290 can be cropped out of the analytical representation 220, so that only the contrast areas within the evaluation zone 290 are evaluated. Of course, the selection of the evaluation zone 290 can also take place before the analytical representation 220 is calculated, in which case the respective zones are cropped out of the digitized images 211, 212, and only the pixel values of the cropped image sections are used for the calculation. This procedure is particularly advantageous if processor units 130 of limited computing power and memory capacity are used.

Instead of calculating the difference in the manner described above, one could also calculate the intersection of a first digitized image 211 and further digitized images 213, 214 of the same series 200. As a next step, the analytical representation 220 is generated by subtracting the pixel values of the intersection from the second digitized image 212. In this analytical representation 220, the moving particles 253A, 253B of the mixture appear again as contrast areas distinguished by different pixel values.

In a further method, the analytical representation 220 is generated by means of an estimate of the movements of the individual pixels of at least two digitized images 211, 212. In the estimate of the movements, all those images whose movement vectors from one image to the other are zero will be characterized as the static image portion. This entails a comparison of the positions of the individual pixels and their pixel values relative to the neighboring pixels and their pixel values, which requires significantly more computing power. The dynamic image portion in this analytical representation 220 is again made up of the moving solid particles 253A, 253B of the mixture, which appear again as contrast areas, i.e. as areas of different pixel values.

Next, the evaluation zone 290 is subdivided into segments 291 of equal size, i.e. equal area. Of course, the segments 291 could also have different sizes and some segments could be removed from further evaluation. This can be necessary for example if individual areas of the container reflect the electromagnetic radiation and the images of the reflective areas lie in the evaluation zone 290, thus representing blind zones.

Figure 3:
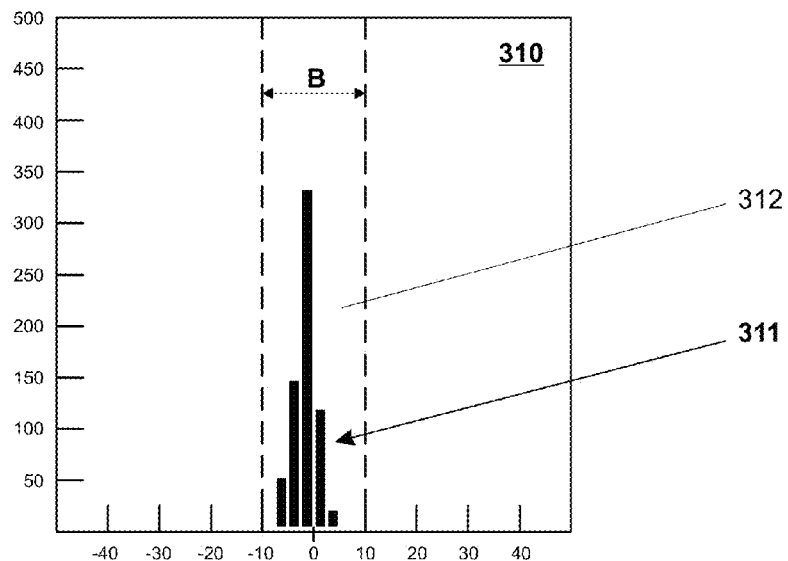
FIG. 3 is a histogram representing a first frequency distribution of pixel values of a segment without contrast areas.
Figure 4:
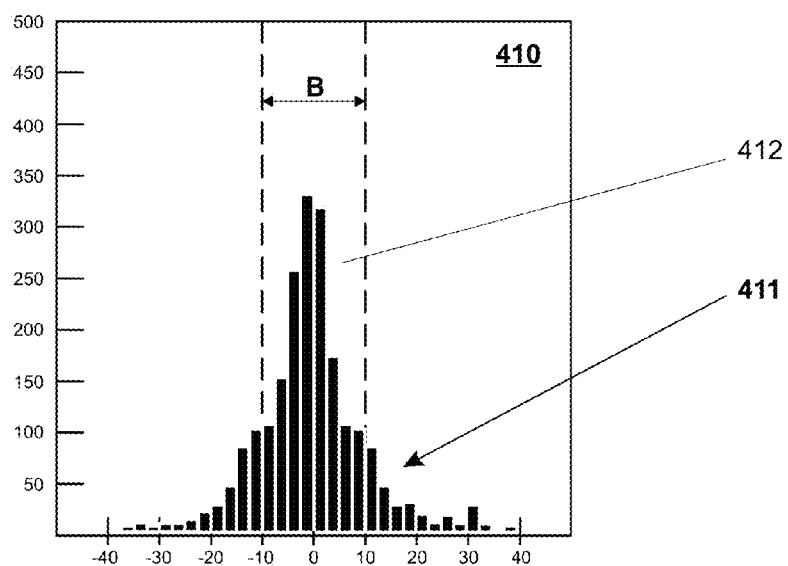
FIG. 4 is a histogram representing a second frequency distribution of pixel values of a segment with contrast areas.

The further evaluation of the individual segment areas 291 is illustrated in FIGS. 3 and 4. FIG. 3 shows a first histogram 310 representing a first frequency distribution 311 of pixel values of a segment, wherein the pixel values appearing in the histogram indicate an absence of contrast areas. The scale on the abscissa marks the pixel values, wherein the median of zero represents gray, positive values represent light, and negative values represent dark pixels. The height of each bar as measured along the ordinate axis represents the number of pixels with the same pixel value. Every camera, more specifically its sensor element, produces an image record in the form of an array of pixel values. Even in the recorded image of a uniformly illuminated monochrome area there are normally some pixel values that deviate from the expected uniformly equal value. These deviations are referred to as camera-related noise and depend essentially on the quality of the camera and also to some degree on the illumination of the object being recorded. Logically, every shadow that is due to a surface irregularity or to inadequate illumination will appear as a faintly visible contrast area in the digital image.

As shown in FIG. 3, in order to eliminate the camera-related noise in the evaluation, a bandwidth 312 of pixel values of the first frequency distribution 311 is excluded from the further evaluation. The predefined bandwidth 312 with the width B is thus also a measure for the sensitivity and the functional reliability of the apparatus. Of course, one could also define a narrower bandwidth 312 and at the same time set a certain allowable maximum for the number of pixels outside of the bandwidth 312. In this case, it is recommended to determine the ratio of the number of pixel values falling outside the bandwidth 312 in relation to the total number of pixels of the segment area 291.

FIG. 4 shows a histogram 410 representing a second frequency distribution 411 of pixel values of a segment area. In comparison to the first frequency distribution 311 the second frequency distribution 411 of FIG. 4 is significantly broader and also includes pixel values outside of the predetermined bandwidth 412. This indicates that the segment represented by the histogram includes contrast areas. The number of segments containing contrast areas can now be counted, and the resultant count represents a measure for the amount of solid substance that is present and/or for the progress of the dissolution process.

In the case where a dissolution process is being monitored, these results together with the material properties of the mixture can be used as the basis for an estimate as to how much longer the mixture needs to be shaken until the solid substance is completely dissolved.

By comparing several analytical representations in their chronological sequence, the declining amount of solid substance and the shrinking of the particle size in the mixture inside the container can be observed and evaluated. By extrapolating the results and using data from previous experience, if available, one can predict the remaining time required to finish the dissolution process.

Figure 5:
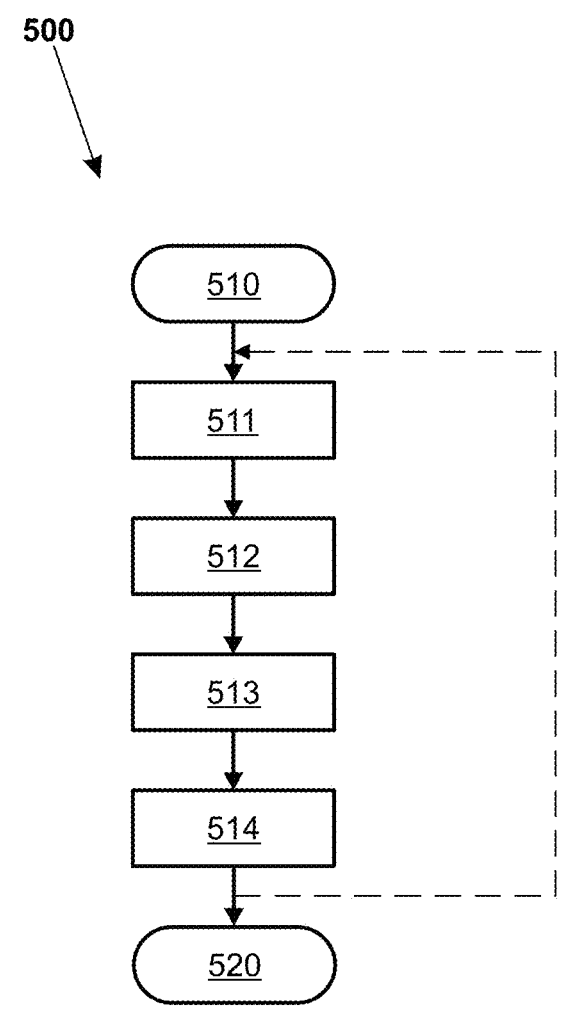
FIG. 5 is a flowchart diagram of the essential procedural steps of the inventive method.

A flowchart diagram 500 with the essential steps of the inventive method is shown in FIG. 5. The method is carried out for example with an apparatus 100 as shown in FIG. 1. In the following description, the features of the apparatus are identified with the reference symbols of FIG. 1, the processing of the digitized images is referenced with the symbols of FIG. 2, and the method steps are identified with the reference symbols of FIG. 5. After the start 510, the container 150, in a first step 511, is set in motion by means of the agitator device 110, whereby kinetic energy is injected into the mixture 258. Next, in a second step 512, the drive mechanism of the agitator device 110 is switched off, whereby the container 150 is made ready for a recording phase, and at least one series 200 of at least two digitized images 211, 212 of the mixture 258 moving around in the now stationary container 150 are taken. In the third step 513, by subtracting one from the other of two digitized images 211, 212, an analytical representation 220 is calculated in which moving parts of the solid substance 153, 253A, 253B appear as contrasting areas, i.e. areas distinguished by having different pixel values. As an alternative to subtracting one from the other of two digitized images 211, 212, the analytical representation 220 can also be obtained through one of the methods described above, using an intersection of a series of digitized images, or also with an estimate of the movements of the individual pixels.

In the fourth step 514, the analytical representation 220 is examined for the presence of contrast areas with different pixel values. When this examination is completed, the sequence of absolutely required steps of the method has reached its end 520. If contrast areas are found in the examination of the analytical representation 220 and if the activity being monitored is a dissolution process, the preceding steps 511, 512, 513, 514 can be repeated until there are no more contrast areas being detected. This loop of repetition is represented by the broken line.

Figure 6:
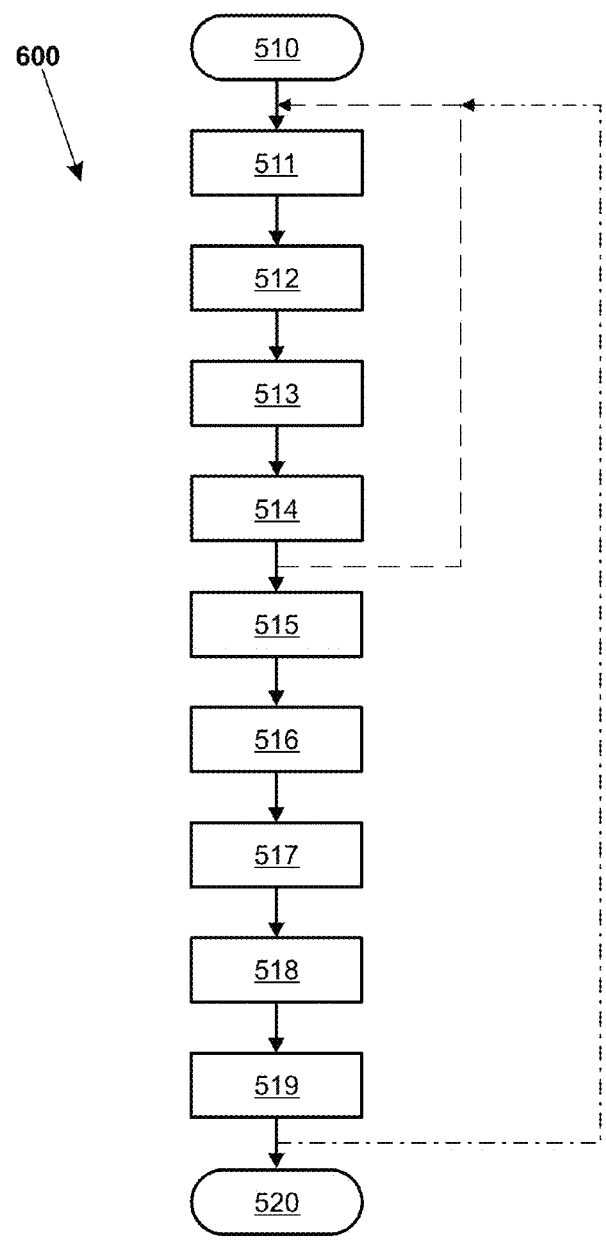
FIG. 6 is a flowchart diagram with additional procedural steps concerning the evaluation.

As shown in FIG. 6, the examination of the analytical representation 220 can be subdivided into further steps. FIG. 6 represents a detailed flowchart diagram 600 of the inventive method with additional possible steps. The entire method can be implemented in a computer program or in firmware, so that the programmed method can be executed step by step by the processor unit. The steps and apparatus features already discussed in the context of FIG. 5 carry the same reference symbols and will not be explained again.

A first addition to the method consists of a fifth step 515 in which at least one evaluation zone 290 is selected within the analytical representation 220, so that unwanted boundary areas such as the gas volume 255 or the liquid surface 257 cannot have a detrimental influence on the evaluation. In a sixth step 516, the evaluation zone 290 is subdivided into segments 291 of equal size. Next, in a seventh step 517, each segment 291 is examined for the presence of contrast areas, i.e. areas distinguished by different pixel values. This is accomplished by evaluating the frequency distribution 311, 411 of the pixel values of a segment area. In order to eliminate camera-related noise, a predetermined pixel value bandwidth 312, 412 of the frequency distribution 311, 411 is disregarded in a further evaluation.

In an eighth step 518, it is now possible to establish the number of segments 291 whose frequency distribution 411 includes pixel values outside of the predetermined pixel value bandwidth 412. The number of segments 291 represents a measure for the amount of solid substance that is present and/or for the progress of the dissolution process.

An even more precise assessment can be reached in a ninth step 519, if the segments 291 whose frequency distributions 411 show pixel values that deviate from the predetermined bandwidth 412 are weighted according to a predetermined plan. The weighting can entail that the number of occurrences of each pixel value is multiplied by a factor, wherein the factor depends on the difference between the respective pixel value and the null-reference value. With the weighting scheme, very dark and very light contrast areas, for example, are given stronger consideration, as they are indicative of large particles. As is generally known, the size of the particles has a strong influence on the dissolution process and in particular on the length of time required for it. The weighted numbers of the segments 291 can subsequently be added up, with the sum of the numbers again representing a measure for the amount of solid substance that is present and/or for the progress of the dissolution process. Of course, based on this more precise evaluation it is possible to determine the direction in which to proceed further. For example, it can be estimated how much longer the shaking needs to be continued until no more contrast areas will be detected. Consequently, the preceding method steps 511, 512, 513, 514, 515, 516, 517, 518, 519 are repeated for a final check that the dissolution is complete. This repeating loop is represented by the dash-dotted line in FIG. 6.

Although the invention has been described through the presentation of specific embodiments, it is considered self-evident that the technical concepts of the invention can also be used in other applications. The apparatus and method of the invention can for example also be used for the monitoring of the mixing process of two or more liquids, if the liquids to be mixed have colors that are distinguishable from each other and/or have distinguishable indices of refraction, so that the still unmixed areas appear as striations in the camera image. The substitution of the solid substance, which has been used hereinabove as an example, by a liquid substance with properties that are optically distinguishable from the liquid phase are therefore within the scope of protection afforded by the claims.

The invention claimed is:

1. An apparatus for dissolving a solid material into a liquid solvent, wherein the solid material and the liquid solvent are enclosed as a mixture in a container with at least one transparent portion, the apparatus comprising:
   an agitator device, adapted to hold the container, and operable to impart movements thereto, thereby injecting kinetic energy into the mixture; and
   a camera, aimed at one of the transparent portions, for taking images of the mixture in motion during a recording phase, the images digitized in the form of arrays of pixels with their associated pixel values;
   a processor unit, operatively connected to each of the agitator device and the camera, the processor unit comprising software programmed to:
   activate the agitator device to inject kinetic energy into the mixture;
   receive from the camera at least one series of at least two digitized images of the mixture moving around inside the container;
   calculate an analytical representation of the mixture by comparing the pixel arrays of the at least two digitized images, such that corresponding areas thereof having different pixel values define contrast areas that represent the moving solid material;
   determine an amount of the solid material remaining undissolved by comparing the calculated analytical representation to a predetermined end amount; and
   repeat the method from the activating step, if the amount of solid material remaining undissolved exceeds the predetermined end amount.

2. The apparatus of claim 1, wherein:
   the software in the processor unit generates the analytical representation by subtracting the pixel values of a first of the received digitized images from the pixel values of a second of the received digitized images, such that the moving solid substance particles of the mixture appear in the analytical representation as contrast areas having different pixel values.

3. The apparatus of claim 2, wherein:
   the software in the processor unit generates the analytical representation by selecting at least one evaluation zone therefrom.

4. The apparatus of claim 3, wherein:
   The software in the processor unit generates the analytical representation by subdividing the at least one evaluation zone into segments of equal or different size.

5. The apparatus of claim 4, wherein:
   the software in the processor unit generates the analytical representation by evaluating a frequency distribution of the pixel values within a segment and by dropping from consideration a predetermined bandwidth of pixel values of the frequency distribution in order to eliminate camera-related noise.

6. The apparatus of claim 1, wherein:
the software in the processor unit generates the analytical representation by calculating an intersection of a series of preceding digitized images by subtracting the pixel values of the intersection from the pixel values of a digitized image, such that the moving solid substance particles of the mixture appear in the analytical representation as contrast areas having different pixel values.

7. The apparatus of claim 1, wherein:
the software in the processor unit generates the analytical representation by estimating the movements of the individual pixels of at least two digitized images, the estimate characterizing as a static image portion all of the pixels whose movement vectors from one to another of the images are zero, characterizing as a dynamic image portion the moving solid substance parts of the mixture that appear in the analytical representation as contrast areas having different pixel values.

8. The apparatus of claim 1, further comprising:
a light source, positioned to aim the light waves therefrom at the transparent portion of the container that is to be captured by the camera.

9. The apparatus of claim 8, wherein:
the light source is an area light source.

10. A method for dissolving a solid material into a liquid solvent, the method comprising the steps of:
attaching, to an agitator, a container having at least one transparent portion and enclosing a mixture of the solid material and the liquid solvent;
activating the agitator, setting the container in motion and injecting kinetic energy into the mixture;
capturing, using a camera, at least one series of at least two digitized images of the mixture moving around inside the container, each digitized image in the form of a pixel array with associated pixel values;
calculating, using a processor unit in communication with the camera, an analytical representation of the mixture by comparing the pixel arrays of the at least two digitized images, such that corresponding areas thereof having different pixel values define contrast areas that represent the moving solid material;
determining an amount of the solid material remaining undissolved in the liquid solvent by examining, using the processor unit, the analytical representation for contrast areas; and
repeating the method from the activating step, as long as the amount of solid material remaining undissolved exceeds a predetermined end amount.

* * * * *